US012776415B2

(12) United States Patent
Seong et al.

(10) Patent No.: US 12,776,415 B2
(45) Date of Patent: Oct. 27, 2026

(54) MRI-BASED METHOD FOR PREDICTING DEGREE OF ACCUMULATION OF BIOMARKER ASSOCIATED WITH ALZHEIMER'S DISEASE AND COMPANION DIAGNOSIS METHOD USING SAME

(71) Applicant: KOREA UNIVERSITY RESEARCH AND BUSINESS FOUNDATION, Seoul (KR)

(72) Inventors: Jun Kyung Seong, Seoul (KR); Wha-Jin Lee, Seoul (KR); Seung-Wook Kim, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 18/836,529

(22) PCT Filed: Jan. 25, 2023

(86) PCT No.: PCT/KR2023/001091
§ 371 (c)(1),
(2) Date: Aug. 7, 2024

(87) PCT Pub. No.: WO2023/153674
PCT Pub. Date: Aug. 17, 2023

(65) Prior Publication Data

US 2025/0166822 A1 May 22, 2025

(30) Foreign Application Priority Data

Feb. 8, 2022 (KR) ........................ 10-2022-0016537

(51) Int. Cl.
*G16H 50/20* (2018.01)
*G16H 10/60* (2018.01)
*G16H 30/40* (2018.01)

(52) U.S. Cl.
CPC ............. *G16H 50/20* (2018.01); *G16H 10/60* (2018.01); *G16H 30/40* (2018.01)

(58) Field of Classification Search
None
See application file for complete search history.

(56) References Cited

U.S. PATENT DOCUMENTS

2002/0087274 A1* 7/2002 Alexander ........... A61B 5/4514 378/3
2003/0031380 A1* 2/2003 Song .............. H04N 21/234381 345/9

(Continued)

FOREIGN PATENT DOCUMENTS

KR 10-1465898 B1 11/2014
KR 10-1757646 B1 7/2017

(Continued)

OTHER PUBLICATIONS

R Ossenkoppele et al. Associations between tau, Aβ, and cortical thickness with cognition in Alzheimer disease. Neurology. Feb. 5, 2019. <URL: https://pubmed.ncbi.nlm.nih.gov/30626656/> (Year: 2019).*

(Continued)

*Primary Examiner* — Bion A Shelden
(74) *Attorney, Agent, or Firm* — Sughrue Mion, PLLC

(57) ABSTRACT

The present invention relates to an MRI-based method for predicting a degree of accumulation of a biomarker associated with Alzheimer's disease and a companion diagnosis method using same, wherein a degree of accumulation of a biomarker associated with Alzheimer's disease in each brain area of a subject can be accurately predicted using positron emission tomography (PET) or in cerebrospinal fluid (CSF) through a lumbar puncture without directly measuring an accumulated level of the biomarker associated with (Continued)

Alzheimer's disease, whereby the present invention can be used for diagnosis and companion diagnosis of various neurodegenerative diseases.

4 Claims, 9 Drawing Sheets

(56) References Cited

U.S. PATENT DOCUMENTS

| | | | | |
|---|---|---|---|---|
| 2021/0090746 | A1* | 3/2021 | Goudey | G16H 50/00 |
| 2021/0313064 | A1* | 10/2021 | Seo | G16B 40/00 |
| 2024/0003918 | A1* | 1/2024 | Reitermann | G16H 50/20 |
| 2024/0225538 | A1* | 7/2024 | Seeley | G16H 30/40 |

FOREIGN PATENT DOCUMENTS

| | | | |
|---|---|---|---|
| KR | 10-2021-0121608 | A | 10/2021 |
| KR | 10-2021-0137830 | A | 11/2021 |
| KR | 10-2321601 | B1 | 11/2021 |

OTHER PUBLICATIONS

International Search Report for PCT/KR2023/001091 dated May 3, 2023 (PCT/ISA/210).

* cited by examiner

MRI-BASED METHOD FOR PREDICTING DEGREE OF ACCUMULATION OF BIOMARKER ASSOCIATED WITH ALZHEIMER'S DISEASE AND COMPANION DIAGNOSIS METHOD USING SAME

CROSS REFERENCE TO RELATED APPLICATIONS

This application is a National Stage of International Application No. PCT/KR2023/001091 filed Jan. 25, 2023, claiming priority based on Korean Patent Application No. 10-2022-0016537 filed Feb. 8, 2022, the entire disclosures of which are incorporated herein by reference.

TECHNICAL FIELD

The present disclosure relates to an MRI-based method for predicting the accumulation of Alzheimer's disease-related biomarkers and a companion diagnostic method using same. More specifically, the present disclosure relates to a method for accurately predicting the accumulation of Alzheimer's disease-related biomarkers in each brain region of a subject without using positron emission tomography (PET) imaging or directly measuring the accumulation of Alzheimer's disease-related biomarkers in cerebrospinal fluid (CSF) obtained by a lumber puncture, and to a companion diagnostic method utilizing same.

BACKGROUND ART

Alzheimer's disease is a chronic neurodegenerative disorder characterized by symptoms such as memory loss, language impairment, and cognitive dysfunction. Pathological hallmarks of Alzheimer's disease include the presence of deposits in brain cells, neural tissues, and blood vessels, neurofibrillary tangles (NFT), amyloid plaques formed by amyloid peptides, tau protein, and synaptic damage. The exact cause of Alzheimer's disease is not completely known, and there is currently no cure. Alzheimer's disease is a common form of dementia and is a leading cause of death along with cardiovascular diseases and cancer. As the average human lifespan increases, the incidence of Alzheimer's disease is also expected to rise.

Traditionally, for the diagnosis of Alzheimer's disease, the accumulation of Alzheimer's disease-related biomarkers such as amyloid and tau is measured using positron emission tomography (PET) imaging or directly measured from cerebrospinal fluid (CSF) obtained by a lumbar puncture. However, PET imaging raises concerns about the side effects due to the injection of radioactive tracers and imposes high costs on patients. The lumbar puncture method is invasive and causes pains to the patient.

Given this background, there is a demand for the development of a method to measure or predict the accumulation of Alzheimer's disease-related biomarkers in each brain region of a subject in a non-invasive and cost-effective manner.

DISCLOSURE OF INVENTION

Technical Problem

The present inventors have developed a method for predicting the accumulation of Alzheimer's disease-related biomarkers without using positron emission tomography (PET) or directly measuring Alzheimer's disease-related biomarkers from cerebrospinal fluid (CSF) obtained by a lumbar puncture. By using the method according to the present disclosure, it was found that the predicted accumulation of Alzheimer's disease-related biomarkers closely matches the actually measured values, demonstrating superior accuracy.

Therefore, the present disclosure aims to provide a method for predicting the accumulation of Alzheimer's disease-related biomarkers using medical imaging.

Also, the present disclosure is to provide a device for predicting the accumulation of Alzheimer's disease-related biomarkers.

Furthermore, the present disclosure is to provide a method for providing information for companion diagnostics related to Alzheimer's treatments.

Yet still, the present disclosure is to provide a device for companion diagnostics related to Alzheimer's treatments.

Solution to Problem

The present disclosure relates to a method for predicting the accumulation of Alzheimer's disease-related biomarkers, based on MRI and a companion diagnostic method using same. The prediction method according to the present disclosure can accurately predict the accumulation of Alzheimer's disease-related biomarkers in brain regions of a subject without using positron emission tomography (PET) imaging or performing a lumbar puncture for obtaining cerebrospinal fluid (CSF).

Below, a detailed description will be given of the present disclosure.

An aspect of the present disclosure provides a method for predicting the accumulation of Alzheimer's disease-related biomarkers using medical imaging, the method including: an acquisition step of acquiring first cerebral cortical thickness data for each region in the brain of a subject; and a prediction step of calculating predicted values of the accumulation of Alzheimer's disease-related biomarkers in each brain region of the subject from the first cerebral cortical thickness data and weight information.

In an embodiment of the present disclosure, the weight is defined based on one or more sets of second cerebral cortical thickness data and one or more sets of biomarker accumulation data.

As used herein, the term "Alzheimer's disease-related biomarker" refers to a substance that can be detected in tissues, organs, or individuals affected by Alzheimer's disease distinguishingly from normal tissues, organs, or individuals and thus allows for the diagnosis of the disease. Specifically, Alzheimer's disease-related biomarkers refer to substances that accumulate in brain regions of subjects affected by Alzheimer's disease. These Alzheimer's disease-related biomarkers may include bio-organic molecules such as proteins, nucleic acids (e.g., mRNA), lipids, glycoproteins, or sugars (monosaccharides, disaccharides, oligosaccharides) that exhibit increased or decreased patterns compared to normal subjects not affected by Alzheimer's disease. Alzheimer's disease-related biomarkers can be measured in PET images and include tau, beta-amyloid, fluorodeoxyglucose, APOE-epsilon4, etc.

The Alzheimer's disease-related biomarkers of the present disclosure may be those measured through PET imaging. Therefore, the present disclosure does not employ PET imaging for Alzheimer's disease-related biomarkers, which have been measured by PET imaging, but can predict levels of Alzheimer's disease-related biomarkers using cerebral cortical thickness information alone, thus reducing the reliance on PET imaging for the diagnosis or treatment of Alzheimer's disease, with the consequent decrease of the cost associated with diagnosis and treatment processes. So long as it is known in the art, any biomarkers measurable via PET imaging may be employed without limitations, as exemplified by beta-amyloid, tau, fluorodeoxyglucose, etc.

The term "weight information", as used herein, refers to specific values or sets of specific values that numerically express the degree of association between the accumulated Alzheimer's disease-related biomarkers in each brain region and the cerebral cortical thickness of the brain region. Thus, the weight information may include weights or sets of weight values. In this regard, the weight can be defined by repeatedly deriving the degree of association between biomarker accumulation data measured in multiple subjects and the cerebral cortical thickness of the same subjects from which corresponding data was measured. Weight information can be defined using a specific model or pattern to calculate the degree of association between Alzheimer's disease-related biomarker accumulation data and cerebral cortical thickness data, such as through correlation analysis or regression analysis. When weights are defined based on correlation analysis or regression analysis, they can be defined as correlation coefficients or regression coefficients. Weight information may include multiple weight values.

The weight information may include information on the degree of association between the accumulation values of Alzheimer's disease-related biomarkers in one brain region and the cerebral cortical thickness of the same or different brain regions. That is, the weight information may include information on the degree of association between the cerebral cortical thickness of each brain region and the accumulation values of Alzheimer's disease-related biomarkers in each brain region.

For example, assuming there are five brain regions, weight information may include information on the degree of association between the accumulation values of Alzheimer's disease-related biomarkers in the first brain region and the cerebral cortical thickness of the first to fifth brain regions (five weights), the degree of association between the accumulation values of Alzheimer's disease-related biomarkers in the second brain region and the cerebral cortical thickness of the first to fifth brain regions (five weights), the degree of association between the accumulation values of Alzheimer's disease-related biomarkers in the third brain region and the cerebral cortical thickness of the first to fifth brain regions (five weights), the degree of association between the accumulation values of Alzheimer's disease-related biomarkers in the fourth brain region and the cerebral cortical thickness of the first to fifth brain regions (five weights), and the degree of association between the accumulation values of Alzheimer's disease-related biomarkers in the fifth brain region and the cerebral cortical thickness of the first to fifth brain regions (five weights).

In an embodiment of the present disclosure, the weight information can be quantified based on the degree of association between the cerebral cortical thickness information of each region of the brain and the accumulation information of Alzheimer's disease-related biomarkers in each region of the brain.

The weight information according to the present disclosure is defined based on at least one set of second cerebral cortical thickness data and at least one set of biomarker accumulation data and may include pre-determined weight information.

In an embodiment of the present disclosure, the Alzheimer's disease-related biomarker may be amyloid and/or tau.

The term "amyloid", as used herein, can interchangeably refer to "amyloid beta" or "Aβ". Amyloid refers to a family of chemically related substances found in the brains, spinal cords, and other tissues of patients with Alzheimer's disease and other neurodegenerative diseases. Amyloid is a fragment of the beta-amyloid precursor protein (APP), which typically includes 38-43 amino acids. In neurodegenerative diseases like Alzheimer's disease, the amount of amyloid accumulated in various brain regions may differ depending on the disease's progression stage. Specifically, amyloid may initially be present in localized brain regions in the early stages of Alzheimer's disease, but can spread to one or more brain regions or even the entire brain as the disease progresses. The method according to an embodiment of the present disclosure uses cerebral cortical thickness data for each region of the subject's brain to predict or calculate the accumulation of amyloid in these regions, thereby facilitating the diagnosis of neurodegenerative diseases such as Alzheimer's disease and providing information on the disease's progression and or the diagnosis of diseases therethrough in the subject.

The term "tau" in this specification refers to a group of abundant central and peripheral nervous system proteins with multiple isoforms, interchangeably referred to as "tau protein". Tau is known to exist in a modified state in brain regions as various neurodegenerative diseases progress. Six major tau isoforms, ranging in size from 352 to 441 amino acids, exist in the human central nervous system (CNS) due to selective splicing. The term "tau" as used herein includes proteins with point mutations, fragments, insertions, deletions, splice variants of full-length wild-type tau, or proteins modified post-translationally, such as phosphorylation. Therefore, in an embodiment of the present disclosure, tau may include phosphorylated tau protein. Similar to amyloid, the method according to an embodiment of the present disclosure uses cerebral cortical thickness data for each region of the subject's brain to predict the accumulation of tau in the specific regions. This allows for identifying the presence and progression of neurodegenerative diseases such Alzheimer's in the subject.

The method according to an embodiment can be used for diagnosing and treating neurodegenerative diseases. Specifically, if the accumulation of Alzheimer's disease-related biomarkers in the subject's brain is predicted according to an embodiment, it is possible to diagnose the presence or progression of a specific neurodegenerative disease.

As used herein, the term "neurodegenerative disease" refers to a condition characterized by reduced or lost function of nerve cells, leading to abnormalities in motor control, cognitive function, sensory function, and autonomic nervous system function. It is used interchangeably with "degenerative neurological disease" and "degenerative brain disease".

As used herein, the term "Alzheimer's disease" refers to a neurodegenerative disorder, including familial and sporadic AD. Typical symptoms of Alzheimer's disease in humans include mild to severe cognitive impairment dementia, progressive memory loss (ranging from mild forgetfulness to severe memory loss and disorientation), impaired spatial skills, personality changes, lack of impulse control, poor judgment, distrust of others, increased stubbornness, restlessness, lack of planning ability, poor decision-making, and social withdrawal, but are not limited thereto. Characteristic pathologies in brain tissue include extracellular amyloid plaques, neurofibrillary tangles, neurite degeneration, granulo-vacuolar degeneration, synapse loss, accumulation of modified tau protein, and widespread neuronal cell death.

The term "prediction", as used herein, refers to estimating the accumulation of Alzheimer's disease-related biomarkers in each brain region or throughout the brain. In the present disclosure, prediction can include the process of quantifying the indirectly estimated accumulation values of Alzheimer's disease-related biomarkers through other parameters, such as cerebral cortical thickness. When the accumulation values or accumulation levels of Alzheimer's disease-related biomarkers are indirectly predicted through cerebral cortical thickness, the term "prediction" may include the meaning of estimation.

The term "subject", as used herein, refers to an entity that has or is suspected of having a neurodegenerative disease, including Alzheimer's disease. In an embodiment of the present disclosure, the subject may be a mammal, for example, may be at least one selected from the group consisting of a human, monkey, dog, cat, mouse, rat, cow, horse, pig, goat, and sheep.

The term "brain region", as used herein, refers to a part of the brain that is sectioned by a specific standard and has a certain volume. In the present disclosure, brain regions can be divided based on various criteria such as function, association, location, structure, and composition of cells for diagnostic purposes and considering the characteristics of the subject. Alternatively, they can be divided using pre-existing partitioning methods. For example, brain regions can be classified by location and function into the primary somatosensory cortex, primary motor cortex, inferior temporal gyrus, superior temporal gyrus, inferior frontal gyrus, anterior cingulate cortex, perirhinal cortex, cortex, etc. Additionally, brain regions can be partitioned according to Brodmann areas, ranging from Brodmann area 1 to Brodmann area 52.

The term "cerebral cortical thickness data", as used herein, refers to data including the measured values of the thickness of the cortical part of the cerebrum in the brain regions of the subject. Cerebral cortical thickness data may include information on the cortical thickness of one or more brain regions. Therefore, cerebral cortical thickness data may include information on the cortical thickness of various brain regions or the entire brain. It is known that cerebral cortical thickness differs between patients with neurodegenerative diseases such as dementia and normal individuals. In the present disclosure, cerebral cortical thickness can be measured directly from the actual brain of the subject or indirectly through imaging techniques. When measured indirectly, it can be assessed using software to analyze magnetic resonance imaging (MRI) data. In an embodiment, cerebral cortical thickness may be first cerebral cortical thickness data used to predict the accumulation of Alzheimer's disease-related biomarkers in the subject's brain or second cerebral cortical thickness data used to derive weight information for calculating the predicted accumulation of Alzheimer's disease-related biomarkers.

In an embodiment of the present disclosure, the biomarker accumulation data may include Alzheimer's disease-related biomarker accumulation data for each brain region measured in the same subjects from which the second cerebral cortical thickness data were obtained.

As used herein, the term "biomarker accumulation data" refers to data including the accumulation values of Alzheimer's disease-related biomarkers accumulated in the brain of a specific subject. Biomarker accumulation data can be used, along with the second cerebral cortical thickness data, to determine the weights accounting for numerical specific values for the degree of association between the accumulation of Alzheimer's disease-related biomarkers and cerebral cortical thickness.

In an embodiment of the present disclosure, the weight information may include information about the degree of association between the cortical thickness of each brain region and the accumulation values of Alzheimer's disease-related biomarkers in each brain region.

In an embodiment of the present disclosure, the acquisition step may involve obtaining first cerebral cortical thickness data for each region of the subject's brain from medical imaging.

In an embodiment of the present disclosure, the first cerebral cortical thickness data may be measured from T1-weighted images of magnetic resonance imaging (MRI).

In an embodiment of the present disclosure, the method may further include a determination step of deriving the degree of association between the second cerebral cortical thickness data and biomarker accumulation data to determine weight information for each brain region.

In an embodiment of the present disclosure, the determination step may include a learning step of determining and training the weight information, based on the second cerebral cortical thickness data and biomarker accumulation data, using machine learning.

As used herein, the term "machine learning" refers to a field of artificial intelligence that includes the field of study that gives computers the capability to learn without being explicitly programmed. Specifically, machine learning may be a technology for researching and constructing a system for learning, predicting, and improving its own performance based on empirical data and an algorithm for the same. Machine learning algorithms construct specific models to make predictions or decisions based on input data rather than executing strictly predefined static program commands. The term "machine learning", as used herein, may be interchangeably used with "machine learning".

Machine learning in the present disclosure may include algorithms such as decision trees, Bayesian networks, support vector machines (SVM), artificial neural networks (ANN), logistic regression, or convolutional neural networks (CNN).

In an embodiment of the present disclosure, the biomarker accumulation data may be obtained from positron emission tomography (PET).

In an embodiment of the present disclosure, the biomarker accumulation data may be converted to Standard Uptake Value Ratio (SUVR) values.

In an embodiment of the present disclosure, the determination step may include an analysis step of calculating the weight information using correlation analysis or regression analysis.

In an embodiment of the present disclosure, the analysis step may include a standardization step of standardizing the correlation coefficients or regression coefficients using demographic or clinical information as covariates.

In an embodiment of the present disclosure, the weight information may be correlation coefficients or regression coefficients.

In an embodiment of the present disclosure, at least one selected from the group consisting of the first cerebral cortical thickness data, second cerebral cortical thickness data, and biomarker accumulation data can be normalized using covariates including age, gender, and years of education.

In an embodiment of the present disclosure, the method may further include a data correction step of normalizing at least one selected from the group consisting of the first cerebral cortical thickness data, second cerebral cortical thickness data, and biomarker accumulation data.

In an embodiment of the present disclosure, the method may be processed by a device, executed by at least one processor, for predicting the accumulation of Alzheimer's disease-related biomarkers in the brain.

In an embodiment of the present disclosure, the prediction step may include a calculation step of calculating the predicted value of the accumulation of Alzheimer's disease-related biomarkers in a specific brain region using the first cerebral cortical thickness data of each of one or more brain regions and the weight defined between the second cerebral cortical thickness data of each brain region included in the one or more brain regions and the biomarker accumulation data of a specific brain region.

In an embodiment of the present disclosure, at least one selected from the group consisting of the acquisition step, prediction step, determination step, data correction step, learning step, standardization step, calculation step, and analysis step may be performed by a computing device.

Another aspect of the present disclosure provides a device for predicting the accumulation of Alzheimer's disease-related biomarkers, the device including: a data acquisition unit for acquiring first cerebral cortical thickness data for each region of the subject's brain; and a prediction unit for calculating predicted values of the accumulation of Alzheimer's disease-related biomarkers in each region of the subject's brain from the first cerebral cortical thickness data by using weight information defined between one or more sets of second cerebral cortical thickness data and one or more sets of biomarker accumulation data.

In an embodiment of the present disclosure, the biomarker accumulation data may be measured in the same subjects from which the second cerebral cortical thickness data were obtained.

In an embodiment of the present disclosure, the first cerebral cortical thickness data may be measured from T1-weighted images of magnetic resonance imaging (MRI).

In an embodiment of the present disclosure, the device may include a weight determination unit for determining weight information by deriving the degree of association between the second cerebral cortical thickness data and the biomarker accumulation data.

In an embodiment of the present disclosure, the device may include a learning unit for determining and training weight information between the second cerebral cortical thickness data and the biomarker accumulation data using machine learning.

In an embodiment of the present disclosure, the weight determination unit may include the learning unit that determines and trains weight information between the second cerebral cortical thickness data and the biomarker accumulation data using machine learning.

In an embodiment of the present disclosure, the biomarker accumulation data may be obtained from positron emission tomography (PET).

In an embodiment of the present disclosure, the biomarker accumulation data may be converted to Standard Uptake Value Ratio (SUVR) values.

In an embodiment of the present disclosure, the weight information may be a correlation coefficient or a regression coefficient.

In an embodiment of the present disclosure, the weight determination unit may include an analysis unit for calculating weight information using correlation analysis or regression analysis.

In an embodiment of the present disclosure, the device may include a data correction unit for correcting at least one set of data selected from the group consisting of the first cerebral cortical thickness data, the second cerebral cortical thickness data, and the biomarker accumulation data.

In an embodiment of the present disclosure, the data correction unit may include a normalization unit for normalizing at least one set of data selected from the group consisting of the first cerebral cortical thickness data, the second cerebral cortical thickness data, and the biomarker accumulation data using covariates including age, gender, and years of education.

In an embodiment of the present disclosure, the device may include a normalization unit for normalizing at least one set of data selected from the group consisting of the first cerebral cortical thickness data, the second cerebral cortical thickness data, and the biomarker accumulation data using covariates including age, gender, and years of education.

In an embodiment of the present disclosure, the analysis unit may standardize the correlation coefficients or regression coefficients using demographic or clinical information as covariates.

Another aspect of the present disclosure pertains to a method for providing information for companion diagnostics related to Alzheimer's disease treatments the method including: an using medical imaging, acquisition step of acquiring first cerebral cortical thickness data for each region of the subject's brain; a prediction step of calculating predicted values of amyloid and tau accumulation in each brain region of the subject using weight information and the first cerebral cortical thickness data; a first calculation step of calculating a first amyloid-tau score from the amyloid interaction value, which scores the interaction between amyloid accumulated in the first brain region and amyloid accumulated in a third brain region adjacent to the first brain region, and the tau predicted value in the first brain region; a second calculation step of calculating a second amyloid-tau score from the predicted values of amyloid and tau in the second brain region of the subject; a first comparison step of comparing the first amyloid-tau score with a first threshold value that distinguishes between positive and negative amyloid and tau in the first brain region; and a second comparison step of comparing the second amyloid-tau score with a second threshold value that distinguishes between positive and negative amyloid and tau in the second brain region.

In an embodiment of the present disclosure, the weight information may be defined between one or more sets of second cerebral cortical thickness data and one or more sets of amyloid-tau data.

In an embodiment of the present disclosure, the amyloid-tau data may include amyloid or tau accumulation data for each brain region measured in the same subjects from which the second cerebral cortical thickness data were obtained.

The term "companion diagnostic", as used herein, refers to a diagnostic method or test used to determine the likelihood of applying a specific therapeutic drug to a particular patient. Companion diagnostics can help select subjects who will respond safely and effectively to the drug and monitor therapeutic effects.

As used herein, the term "companion diagnostic for Alzheimer's disease treatments" refers to a method or test for determining the progression stage of Alzheimer's disease in a subject by analyzing the interaction between amyloid and tau proteins, thereby determining the appropriate therapeutic drug for the subject. Companion diagnostics for Alzheimer's disease treatments may be carried out by defining remote interaction scores between amyloid and tau in one brain region and an adjacent brain region, and local interaction scores between amyloid and tau in another brain region, and diagnosing the disease progression stage of Alzheimer's disease based on the two defined scores. In addition, an optimal therapeutic drug for the subject can be determined based on the two defined scores and the disease progression stage.

As used herein, the term "amyloid-tau data" refers to data including the accumulation values of amyloid and/or tau accumulated in the brain of a specific subject. The amyloid-tau data can be used, along with the second cerebral cortical thickness data, to determine weights that quantify the degree of association between the accumulation of amyloid and tau and the cerebral cortical thickness. The amyloid-tau data may include both the data of amyloid accumulation and tau accumulation in a specific individual or only the accumulation data of either amyloid or tau. The amyloid-tau data may include data of amyloid and/or tau accumulation in each brain region of a specific subject or data of amyloid and/or tau accumulation throughout the entire brain of the subject.

The term "amyloid-tau score", as used herein, refers to a score quantifying the remote interaction between amyloid and tau in a specific brain region and a brain region adjacent thereto, or the local interaction between amyloid and tau in a specific brain region. In this regard, the score quantifying the remote interaction can be referred to as the first amyloid-tau score, and the score quantifying the local interaction can be referred to as the second amyloid-tau score. The amyloid-tau score for remote interaction can be calculated in various ways, such as based on the degree of interaction between amyloid accumulated in a specific brain region and a brain region adjacent to the specific brain region, and the accumulation degree of tau in the specific brain region. The adjacent brain region may include one or more brain regions. The amyloid-tau score for local interaction can also be calculated in various ways, such as based on the degree of amyloid accumulation and tau accumulation in a specific brain region.

The term "amyloid interaction value", as used herein, refers to a value quantifying the interaction between amyloid accumulated in a specific brain region and a brain region adjacent to the specific brain region. The amyloid interaction value can be calculated from the strength or connectivity of neural networks between a specific brain region and a brain region adjacent to the specific brain region and the accumulation values of amyloid in both brain regions.

The term "threshold value", as used herein, refers to a numerical value that most accurately distinguishes between positive and negative amyloid and/or tau in a specific brain region. The threshold value may account for the accumulation value of amyloid and/or tau at the reference point where normal groups are discriminated from disease groups based on the accumulation data of amyloid and/or tau in normal groups, Alzheimer's disease patients, and patients with mild cognitive impairment.

In an embodiment of the present disclosure, the amyloid interaction value may be calculated from the amyloid accumulation values of the first and the third brain region and the neural network weight values.

In the present disclosure, the neural network weight may be derived from the strength of the neural network between the first and third brain regions. For instance, the neural network weight may be the region-specific weight for amyloid between the first and third brain regions.

In an embodiment of the present disclosure, the method may further include a classification step of classifying the subject into group 1 if the first amyloid-tau score is less than or equal to the first threshold value, group 2 if the first amyloid-tau score exceeds the first threshold value and the second amyloid-tau score is less than or equal to the second threshold value, and group 3 if the second amyloid-tau score exceeds the second threshold value.

In the present disclosure, group 1 may be a set of normal subjects, group 2 may be a set of subjects with amnestic mild cognitive impairment (aMCI), and group 3 may a set of subjects with Alzheimer's disease.

Another aspect of the present disclosure pertains to a companion diagnostic device for Alzheimer's disease, the device including: a data acquisition unit for acquiring first cerebral cortical thickness data for each region of the subject's brain; a prediction unit for calculating predicted values of amyloid and tau accumulation in each brain region of the subject using weight information and the first cerebral cortical thickness data; a first calculation unit for calculating a first amyloid-tau score from the amyloid interaction value, which scores the interaction between amyloid accumulated in a first brain region and a third brain region adjacent to the first brain region, and a tau accumulation value in the first brain region; a second calculation unit for calculating a second amyloid-tau score from the amyloid and tau accumulation values in a second brain region of the subject; a first comparison unit for comparing the first amyloid-tau score with a first threshold value that distinguishes between positive and negative amyloid and/or tau in the first brain region; and a second comparison unit for comparing the second amyloid-tau score with a second threshold value that distinguishes between positive and negative amyloid and/or tau in the second brain region.

In an embodiment of the present disclosure, the amyloid-tau data may include amyloid and/or tau accumulation data for each brain region measured in the same subjects from which the second cerebral cortical thickness data were obtained.

In an embodiment of the present disclosure, the weight information may be defined between one or more sets of second cerebral cortical thickness data and one or more sets of amyloid-tau data.

In an embodiment of the present disclosure, the first cerebral cortical thickness data may be measured from T1-weighted images of magnetic resonance imaging (MRI).

In an embodiment of the present disclosure, the device may include a weight determination unit for determining weight information for each brain region by deriving the degree of association between the second cerebral cortical thickness data and the amyloid-tau data.

In an embodiment of the present disclosure, the device may include a learning unit for determining and training weight information between the second cerebral cortical thickness data and the amyloid-tau data using machine learning.

In an embodiment of the present disclosure, the weight determination unit may include the learning unit for determining and training weight information between the second cerebral cortical thickness data and the amyloid-tau data using machine learning.

In an embodiment of the present disclosure, the amyloid-tau data may be obtained from positron emission tomography.

In an embodiment of the present disclosure, the amyloid-tau data may be converted to Standard Uptake Value Ratio (SUVR) values.

In an embodiment of the present disclosure, the weight information may be a correlation coefficient or a regression coefficient.

In an embodiment of the present disclosure, the weight determination unit may include an analysis unit for calculating weight correlation using analysis or regression analysis.

In an embodiment of the present disclosure, the device may include a data correction unit for correcting at least one set of data selected from the group consisting of the first cerebral cortical thickness data, the second cerebral cortical thickness data, and the amyloid-tau data.

In an embodiment of the present disclosure, the data correction unit may include a normalization unit for normalizing at least one set of data selected from the group consisting of the first cerebral cortical thickness data, the second cerebral cortical thickness data, and the amyloid-tau data by using covariates including age, gender, and years of education.

In an embodiment of the present disclosure, the device may include a normalization unit for normalizing at least one set of data selected from the group consisting of the first cerebral cortical thickness data, the second cerebral cortical thickness data, and the amyloid-tau data by using covariates including age, gender, and years of education.

In an embodiment of the present disclosure, the analysis unit may standardize the correlation coefficients or regression coefficients using demographic or clinical information as covariates.

In an embodiment of the present disclosure, the amyloid interaction value may be calculated from the amyloid accumulation values of the first and third brain regions and the neural network weight values.

In an embodiment of the present disclosure, the device may further a classification unit for classifying the subject into group 1 if the first amyloid-tau score is less than or equal to the first threshold value; into group 2 if the first amyloid-tau score exceeds the first threshold value and the second amyloid-tau score is less than or equal to the second threshold value; and into group 3 if the second amyloid-tau score exceeds the second threshold value.

Advantageous Effects of Invention

The present disclosure relates to a method for predicting the accumulation of Alzheimer's disease-related biomarkers based on MRI and a companion diagnostic method using same. With the ability to accurate prediction of the accumulation of Alzheimer's disease-related biomarkers in specific brain regions of a subject without using positron emission tomography (PET) imaging or directly measuring the accumulation of values Alzheimer's disease-related biomarkers from cerebrospinal fluid (CSF) obtained by a lumbar puncture, the method can be utilized for the diagnosis and companion diagnostics of various neurodegenerative diseases.

Figure 1:
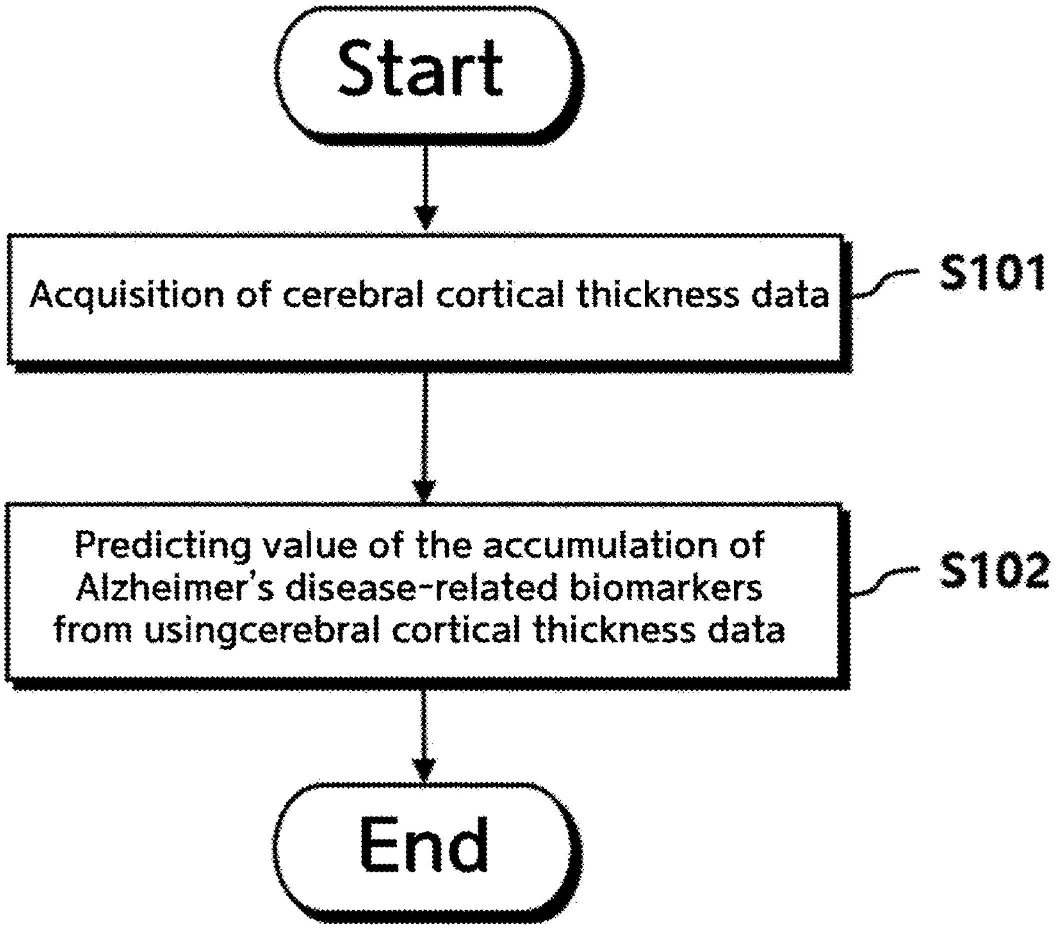
FIG. 1 is a block diagram illustrating the process of predicting the accumulation values of Alzheimer's disease-related biomarkers according to an embodiment of the present disclosure.

BEST MODE FOR CARRYING OUT THE INVENTION the Hereinafter, the embodiments of present disclosure will be described in detail with reference to the accompanying drawings so that those skilled in the art to which the present disclosure pertains can easily implement them. However, the present disclosure can be embodied in various different forms and is not limited to the embodiments described herein. Parts not related to the description have been omitted from the drawings to clearly describe the present disclosure, and similar parts are denoted by similar reference numerals throughout the specification.

In the specification, when a part is said to "include" a certain component, it means that other components can be included unless otherwise stated. The terms "and/or" and "or" include any combination and all combinations of the listed items.

Furthermore, the terms "unit" and "module" described in the specification refer to a unit that processes at least one function or operation and can be implemented as hardware, software, or a combination of both.

It should be understood that various illustrative logical blocks, configurations, modules, circuits, means, logics, and algorithm steps described in connection with the embodiments disclosed herein can be implemented as electronic hardware, computer software, or combinations of both. To clearly illustrate the interchangeability of hardware and software, various illustrative components, blocks, configurations, means, logics, modules, circuits, and steps have been described generally in terms of their functionality. Whether such functionality is implemented as hardware or software depends on the specific application and design constraints imposed on the overall system. Skilled artisans can implement the described functionality in varying ways for each specific application but such implementation decisions should not be interpreted as departing from the scope of this disclosure.

FIG. 1 is a block diagram illustrating a process of predicting the accumulation values of Alzheimer's disease-related biomarkers according to an embodiment of the present disclosure.

Referring to FIG. 1, a method for predicting the accumulation degree of Alzheimer's disease-related biomarkers according to an embodiment of the present disclosure involves acquiring cerebral cortical thickness data and using same to predict the accumulation values of Alzheimer's disease-related biomarkers.

The cerebral cortical thickness data obtained in step S101 (hereinafter referred to as "first cerebral cortical thickness data") includes cerebral cortical thickness information of the subject whose Alzheimer's disease-related biomarker accumulation is to be predicted.

The first cerebral cortical thickness data may be acquired from medical imaging.

The first cerebral cortical thickness data obtained in step S101 may be measured from magnetic resonance imaging (MRI). Specifically, the first cerebral cortical thickness data obtained in step S101 may be measured from T1- or T2-weighted MRI data. For example, the first cerebral cortical thickness data may be measured from T1-weighted MRI data. The acquired first cerebral cortical thickness data may include information on the cortical thickness of the entire brain or the cerebral cortical thickness information for each region of the brain.

Cerebral cortical thickness information may be measured from MRI using a software program. For example, the FreeSurfer program may be used as the software program. Therefore, the first cerebral cortical thickness data can be generated by generating the pial/white surface from the MRI through the program, extracting the cortical portion, obtaining the thickness of the cortical portion at each vertex defined on the surface, and calculating the average thickness of the vertices corresponding to each brain region.

Using the first cerebral cortical thickness data obtained in step S101, the accumulation values of Alzheimer's disease-related biomarkers may be predicted or calculated in step S102. Specifically, the accumulation values of Alzheimer's disease-related biomarkers may be predicted or calculated from the cerebral cortical thickness data f the subject by considering the degree of association between cerebral cortical thickness and biomarker accumulation data.

At this time, the degree of association between cerebral cortical thickness data and biomarker accumulation data may be expressed as weight information. The weight information may be defined between cerebral cortical thickness data (hereinafter referred to as "second cerebral cortical thickness data") separate from the cerebral cortical thickness data of the subject whose Alzheimer's disease-related biomarker accumulation is to be predicted and the biomarker accumulation data measured from the same subject from which the second cerebral cortical thickness data was obtained. In this regard, the second cerebral cortical thickness data may be measured from T1-weighted MRI, and the biomarker accumulation data can be obtained from positron emission tomography (PET).

The weight information may be defined between the second cerebral cortical thickness of each brain region and the biomarker accumulation data of each brain region. In this context, the weight information may represent a set of numerical values indicating the degree of association between the accumulation value of Alzheimer's disease-related biomarkers in one brain region and the cerebral cortical thickness data of the same or different brain regions. Therefore, when predicting the accumulation value of Alzheimer's disease-related biomarkers in a single brain region, multiple weights may be utilized.

For example, consider the case of predicting the accumulation degree of Alzheimer's disease-related biomarkers in the inferior temporal gyrus (ITG) using the first cerebral cortical thickness data obtained from a subject. In this case, the accumulation degree of Alzheimer's disease-related biomarkers in the ITG region may be predicted using the weight information defined between the second cerebral cortical thickness data of the ITG region and the biomarker accumulation data of the ITG region, as well as the first cerebral cortical thickness data of the ITG region.

Alternatively, the accumulation of Alzheimer's disease-related biomarkers in the ITG region may be predicted from the cerebral cortical thickness data of multiple brain regions and the weight information between each of these brain regions and the ITG region (where the weight information may be defined between the second cerebral cortical thickness data of each brain region and the biomarker accumulation data of the ITG region). In this case, the multiple brain regions may not include the ITG region. In other words, the weights defined between the cerebral cortical thickness of the ITG region and the biomarker accumulation data of the ITG region may not be used.

The second cerebral cortical thickness data and the biomarker accumulation data measured from the same subjects may consist of multiple pairs. For example, the second cerebral cortical thickness data and the biomarker accumulation data measured from the same subjects may be 10 pairs, 20 pairs, 30 pairs, 50 pairs, 100 pairs, 200 pairs, 500 pairs, 1000 pairs, 1500 pairs, 3000 pairs, or more than 10,000 pairs. In an embodiment, the weights may be improved in accuracy by deriving the degree of association from multiple pairs of second cerebral cortical thickness data and biomarker accumulation data. Consequently, using more pairs of second cerebral cortical thickness data and biomarker accumulation data for defining the weights can improve the accuracy of the defined weight information, thereby enhancing the accuracy of predicting the accumulation of Alzheimer's disease-related biomarkers using the weight information.

The method for predicting the accumulation degree of Alzheimer's disease-related biomarkers according to an embodiment can predict the accumulation of Alzheimer's disease-related biomarkers in 'each region' of the brain Therefore, when the accumulation as described above values of Alzheimer's disease-related biomarkers are predicted for each region of the brain, it is advantageously possible not only to determine the presence of Alzheimer's disease in the subject but also to diagnose the progression stage of Alzheimer's disease based on the accumulation degree of Alzheimer's disease-related biomarkers in each brain region.

In the present disclosure, the Alzheimer's disease-related biomarker may include amyloid or tau. Amyloid is known to be observed in most degenerative neurological diseases, including Parkinson's disease (PD) and transmissible spongiform encephalopathy (TSE), while tau is known to be observed in degenerative neurological diseases such as frontotemporal dementia (FTD), progressive supranuclear palsy (PSP), Pick's disease, and chronic traumatic encephalopathy (CTE). Therefore, the method for predicting the accumulation values of Alzheimer's disease-related biomarkers in each brain region according to an embodiment can be used to diagnose various degenerative neurological diseases. Furthermore, the method for providing information for companion diagnostics for Alzheimer's treatments according to an embodiment, which will be described later, also selects the optimal therapeutic agent through companion diagnostics based on the predicted accumulation values of amyloid and/or tau in each brain region. Therefore, the method for predicting the accumulation degree of Alzheimer's disease-related biomarkers in each brain region according to an embodiment can be widely used not only in the diagnosis of neurodegenerative diseases but also in the overall treatment of neurodegenerative diseases, including the selection of therapeutic agents.

In the method for predicting the accumulation values of Alzheimer's disease-related biomarkers according to an embodiment, pre-defined weight information may be used as the weight information. Therefore, the method for predicting the accumulation degree of Alzheimer's disease-related biomarkers according to an embodiment may not include the step of determining weight information, and the process of predicting the accumulation values of Alzheimer's disease-related biomarkers and the process of determining (defining) weight information may be performed separately.

In step S102, the accumulation degree of Alzheimer's disease-related biomarkers in a region to be predicted may be calculated from the cerebral cortical thickness data of that region using the weight information defined for the region.

Alternatively, the predicted value of the of Alzheimer's disease-related accumulation degree biomarkers in a brain region to be predicted may be calculated from the cerebral cortical thickness data of one or more brain regions and the weight information defined between the cerebral cortical thickness data of each of the one or more brain regions and the biomarker accumulation data of the brain region to be predicted. Specifically, the predicted value of the accumulation degree of Alzheimer's disease-related biomarkers in a brain region to be predicted can be calculated by summing the product of the weights defined between the cerebral cortical thickness data of each of the one or more brain regions and the biomarker accumulation data of a brain region to be predicted and the cerebral cortical thickness data of each of the one or more brain regions.

For example, the accumulation value of Alzheimer's disease-related biomarkers can be calculated using the following mathematical formula:

$$pX_i = \sum_{j=1}^{m} a_j \hat{\beta}_{ij}$$ [Mathematical Formula 1]

[wherein, $pX_i$ is the predicted accumulation degree of Alzheimer's disease-related biomarkers (i may represent a specific region or the entire brain), m is the number of regions used to predict the accumulation value of Alzheimer's disease-related biomarkers, $a_j$ is the cerebral cortical thickness of the selected region, and $\hat{\beta}_{ij}$ is the weight for the region to be predicted for the accumulation value of Alzheimer's disease-related biomarkers]

The method for predicting the accumulation values of Alzheimer's disease-related biomarkers according to an embodiment may include a data normalization step of normalizing at least one selected from the group consisting of first cerebral cortical thickness data, second cerebral cortical thickness data, and biomarker accumulation data.

When the data normalization step is included, the first cerebral cortical thickness data, second cerebral cortical thickness data, and biomarker accumulation data may be normalized, ensuring that each data point is reflected with the same importance in the prediction of Alzheimer's disease-related biomarker accumulation.

Figure 2:
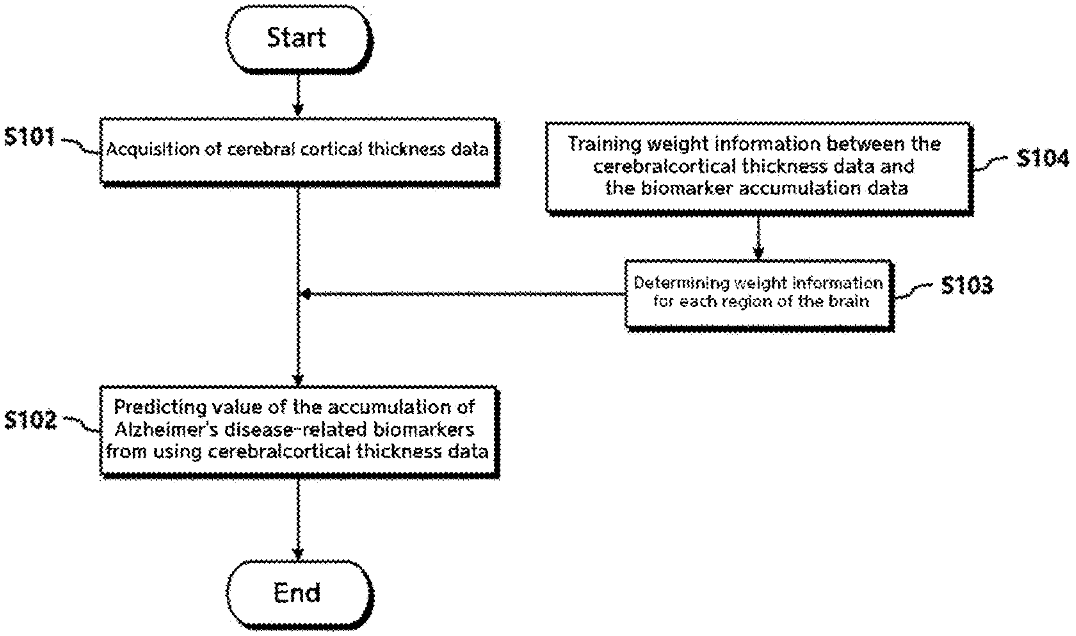
FIG. 2 is a block diagram illustrating the process of predicting the accumulation values of Alzheimer's disease-related biomarkers according to another embodiment of the present disclosure.

FIG. 2 is a block diagram illustrating the process of predicting the accumulation values of Alzheimer's disease-related biomarkers according to another embodiment of the present disclosure.

Referring to FIG. 2, the method for predicting the accumulation degree of Alzheimer's disease-related biomarkers according to another embodiment involves acquiring cerebral cortical thickness data, determining weight information between the cerebral cortical thickness data and Alzheimer's disease-related biomarker accumulation data, and using the weight information to predict or calculate the accumulation values of Alzheimer's disease-related biomarkers.

In step S103, weight information for each brain region can be defined through the degree of association between the second cerebral cortical thickness data and the biomarker accumulation data for each brain region.

The biomarker accumulation data may be obtained using positron emission tomography (PET) imaging or from cerebrospinal fluid (CSF) obtained by a lumbar puncture. When acquiring Alzheimer's disease-related biomarker accumulation data for each brain region, PET imaging may be utilized. When obtaining biomarker accumulation data through PET imaging, the biomarker accumulation data may be expressed as Standard Uptake Value Ratio (SUVR) values. SUVR values can be calculated by extracting standardized uptake values (SUVs) from PET images aligned with T1-weighted MRI images of the same subject using a linear registration method and then calculating the ratio of these values to the value in a reference region.

Weight information can be defined by obtaining a model for the degree of association between cerebral cortical thickness and Alzheimer's disease-related biomarker accumulation values and then measuring the goodness of fit. The weights can be defined using mathematical models known in the art. For example, weight information can be defined using a linear regression model, logistic regression model, ridge regression model, lasso regression, or polynomial regression model, but is not limited to these. When weight information is defined through regression analysis, the weights included in the weight information can be expressed as regression coefficients.

In step S103, the weight information may be defined by correlation analysis or regression analysis using the degree of association. When weight information is defined through correlation analysis, the weights can be expressed as correlation coefficients, where a larger absolute value indicates a more significant association.

For example, the weights according to an embodiment can be defined using the following mathematical formula 2:

$$H(X) = \frac{1}{1+e^{-(Wx+b)}} = \text{sigmoid}(Wx+b) = \sigma(Wx+b)$$ [Mathematical Formula 2]

(where sigmoid is a sigmoid function that produces an output value between 0 and 1 for any input value, W represents a weight that best fits the given data, and b represents the bias (intercept)).

Weight information can be defined using a machine learning model or deep learning model. The machine learning models or deep learning model may be pre-trained or established through a training process using one or more sets of second cerebral cortical thickness data and one or more sets of biomarker accumulation data.

When machine learning is used, the machine learning model may include algorithms such as decision trees, Bayesian networks, or support vector machines (SVM).

When deep learning models are used, the deep learning model may be a deep neural network (DNN), which includes a neural network with multiple hidden layers in addition to the input and output layers. Using deep neural networks helps in identifying latent structures in the data. The deep neural network may include convolutional neural networks (CNN), recurrent neural networks (RNN), restricted Boltzmann machines (RBM), deep belief networks (DBN), Q-networks, U-networks, and Siamese networks, among others.

When the weight determination process is performed using machine learning or deep learning, the accuracy of determining weight information for each brain region through the algorithm model can be improved as the learning of the association between cerebral cortical thickness data and biomarker accumulation data is repeatedly carried out.

In the method for predicting the accumulation degree of Alzheimer's disease-related biomarkers in the brain according to an embodiment, a data correction step may be performed to normalize at least one set of data selected from the group consisting of first cerebral cortical thickness data, second cerebral cortical thickness data, and biomarker accumulation data (not shown). The first cerebral cortical thickness data, second cerebral cortical thickness data, and biomarker accumulation data may be reflected with the same importance through the data correction process.

In this case, demographic information or clinical information, including age, sex, and years of education, may be used as covariates in the data correction process. For example, data standardization may be expressed as a W-score, which can be derived using the following mathematical formula 3:

$$W-\text{score}_i = \frac{E_i - \hat{E}_i}{\sqrt{\text{Var}(E_{CN,i} - \hat{E}_{CN,i})}} \quad \text{[Mathematical Formula 3]}$$

(wherein, $E_i$ is data to be standardized, including cerebral cortical thickness and the accumulation values of Alzheimer's disease-related biomarkers in region i, $\hat{E}_i$ is the predicted data for region i using only the covariates through a regression model between covariates and values to be standardized in a normal group, and $\sqrt{\text{Var}(E_{CN,i}-\hat{E}_{CN,i})}$ is the residual standard deviation between the actual data for region i and the predicted values from the regression model in the normal group.)

Figure 3:
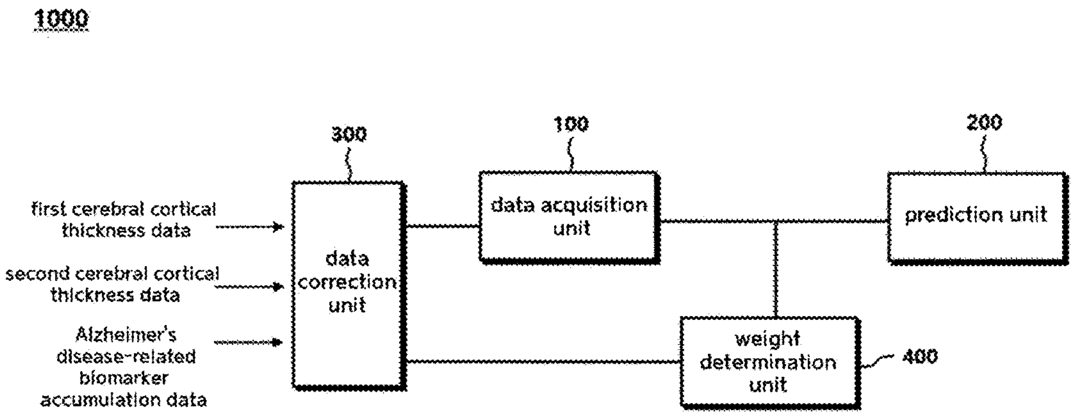
FIG. 3 is a block diagram illustrating a computing device performing the operations for predicting the accumulation values of Alzheimer's disease-related biomarkers according to an embodiment of the present disclosure.

FIG. 3 is a block diagram illustrating a computing device performing the operations for predicting the accumulation values of Alzheimer's disease-related biomarkers according to an embodiment of the present disclosure.

Referring to FIG. 3, the device for predicting the accumulation degree of Alzheimer's disease-related biomarkers according to an embodiment includes a data acquisition unit (100), a prediction unit (200), a data correction unit (300), and a weight determination unit (400).

The data acquisition unit (100) is responsible for acquiring the first cerebral cortical thickness data. The first cerebral cortical thickness data can be corrected and converted into normalized values by the data correction unit (300), and then transmitted back to the data acquisition unit (100).

The prediction unit (200) may use the first cerebral cortical thickness data transmitted from the data acquisition unit (100) and the weight information provided by the weight determination unit (400) to predict or calculate the accumulation values of Alzheimer's disease-related biomarkers in the subject's brain regions. The accumulation values of Alzheimer's disease-related biomarkers may be calculated using the cerebral cortical thickness data of one or more brain regions and the weight information defined between the cerebral cortical thickness data of each of these brain regions and the biomarker accumulation data of the brain region to be predicted. Specifically, the predicted accumulation value of Alzheimer's disease-related biomarkers in the brain region can be calculated by summing the products of the weights defined between the cerebral cortical thickness data of each of the one or more brain regions and the biomarker accumulation data of the brain region to be predicted, and the cerebral cortical thickness data of each of the one or more brain regions.

For example, the accumulation value of Alzheimer's disease-related biomarkers can be calculated using the following mathematical formula 1:

$$pX_i = \sum_{j=1}^{m} a_j \hat{\beta}_{ij} \quad \text{[Mathematical Formula 1]}$$

[wherein, $pX_i$ is the predicted accumulation degree of Alzheimer's disease-related biomarkers (i may represent a specific region or the entire brain), m is the number of regions used to predict the accumulation value of Alzheimer's disease-related biomarkers, $a_j$ is the cerebral cortical thickness of the selected region, and $\hat{\beta}_{ij}$ is the weight for the region to be predicted for the accumulation value of Alzheimer's disease-related biomarkers]

The data correction unit (300) may receive the first cerebral cortical thickness data, second cerebral cortical thickness data, and biomarker accumulation data. The first cerebral cortical thickness data, second cerebral cortical thickness data, and biomarker accumulation data may be normalized through the data correction unit.

The data correction unit (300) can use demographic information or clinical information, including age, gender, and years of education, as covariates to correct the data. For example, data standardization can be expressed as a W-score, which can be derived using the following mathematical formula 3:

$$W-\text{score}_i = \frac{E_i - \hat{E}_i}{\sqrt{\text{Var}(E_{CN,i} - \hat{E}_{CN,i})}} \quad \text{[Mathematical Formula 3]}$$

(wherein, $E_i$ is data to be standardized, including cerebral cortical thickness and the accumulation values of Alzheimer's disease-related biomarkers in region i, $\hat{E}_i$ is the predicted data for region i using only the covariates through a regression model between covariates and values to be standardized in a normal group, and $\sqrt{Var(E_{CN,i}-\hat{E}_{CN,i})}$ is the residual standard deviation between the actual data for region i and the predicted values from the regression model in the normal group.)

The weight determination unit (400) may receive the second cerebral cortical thickness data and biomarker accumulation data. Alternatively, the weight determination unit (400) may receive the corrected first cerebral cortical thickness data, second cerebral cortical thickness data, and biomarker accumulation data from the data correction unit (300).

The weight determination unit (400) may derive the degree of association between the second cerebral cortical thickness data and the biomarker accumulation data for each brain region. The degree of association can be then calculated as specific numerical values, i.e., weights.

The weight determination unit (400) may include a learning unit that determines and learns weight information between the second cerebral cortical thickness data and the biomarker accumulation data using deep learning or machine learning.

When the learning unit determines and learns the weights using machine learning, it can use machine learning models known in the art. For example, the learning unit can include algorithms such as decision trees, Bayesian networks, or support vector machines (SVM) as machine learning models.

When the learning unit determines and learns the weights using deep learning models, it can use deep learning models known in the art. For example, the learning unit can include deep neural network algorithms as deep learning models.

The computing device for performing operations to predict the accumulation degree of Alzheimer's disease-related biomarkers according to an embodiment of the present disclosure may further include a communication unit for transmitting and receiving brain images and other data, and a database for storing and managing the data used in brain imaging and other computing processes. Therefore, the computing device for performing operations to predict the accumulation degree of Alzheimer's disease-related biomarkers according to an embodiment may be capable of wired or wireless communication with brain imaging devices such as MRI scanners and PET scanners. Additionally, data such as weight data, cerebral cortical thickness data, and biomarker accumulation data can be stored in the database. The data stored in the database can be managed (e.g., deleted, modified) based on authorized external input from a user.

The computing device for performing operations to predict the accumulation degree of Alzheimer's disease-related biomarkers according to an embodiment of the present disclosure may further include a visual display device capable of visually displaying the predicted accumulation values of Alzheimer's disease-related biomarkers. The visual display device may be an electronic device capable of processing and outputting images, and can electronically communicate with the communication unit. The visual display device may be a desktop, smartphone, mobile phone, videophone, laptop PC, digital camera, wearable device, medical device, or tablet PC, but is not limited thereto.

Figure 4:
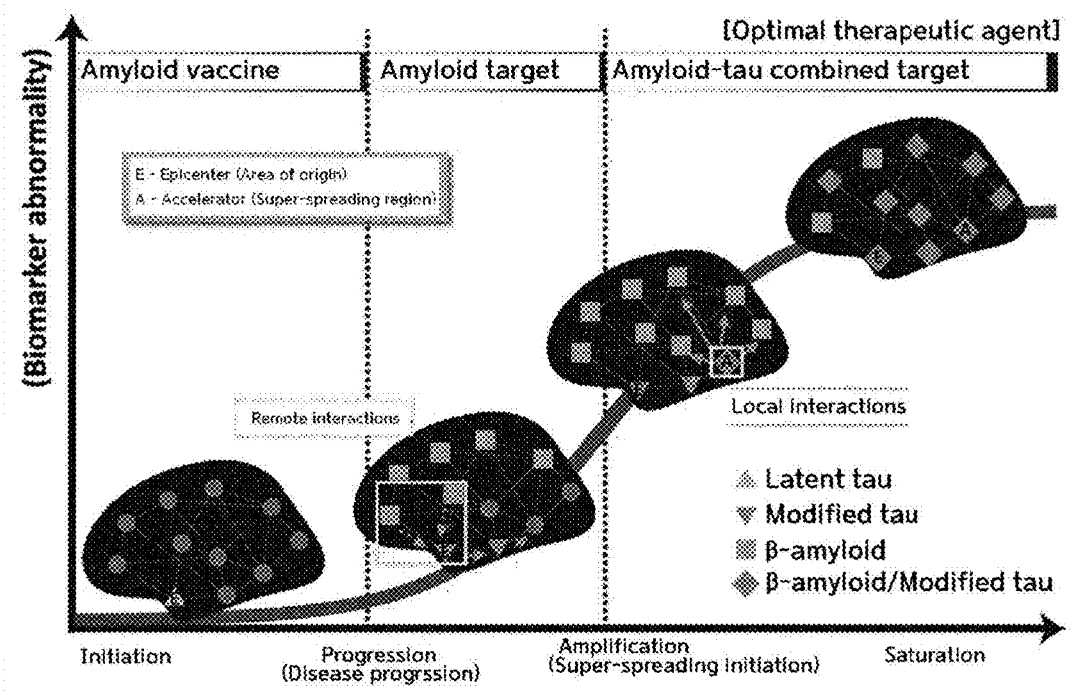
FIG. 4 is a diagram illustrating the modification and propagation processes of amyloid and tau according to the disease progression of Alzheimer's.

FIG. 4 is a diagram illustrating the modification and propagation processes of amyloid and tau according to the disease progression of Alzheimer's disease.

Referring to FIG. 4, Alzheimer's disease may progress based on the interaction between amyloid and tau, and the interaction pattern between amyloid and tau may vary depending on the disease progression stage. Specifically, in the early stages of Alzheimer's disease, tau proteins present in specific brain regions can interact remotely with amyloid in adjacent brain regions. Amyloid and/or tau present in specific brain regions can undergo modifications through interactions with adjacent amyloid, leading to changes in tau in specific regions. When tau is modified, locally present tau can propagate to adjacent regions, leading to the accumulation of modified tau proteins in adjacent regions. As tau proteins continuously accumulate in adjacent brain regions, modified tau proteins can accumulate in brain regions where amyloid is present. At this stage, local interactions between the modified tau proteins and amyloid can occur in the affected brain regions. When local interactions between amyloid and tau occur, this can induce the accumulation of beta-amyloid and modified tau proteins in adjacent brain regions, leading to the accumulation of modified tau proteins and amyloid throughout the brain. Therefore, in the early stages of Alzheimer's disease, remote interactions between amyloid and tau in adjacent brain regions can be the main cause of disease progression, while local interactions between amyloid and tau in the affected brain regions become the main cause as the disease progresses.

From a therapeutic perspective, the interactions between amyloid and tau may be important factors in selecting appropriate therapeutic agents for Alzheimer's treatment. For example, in the early stages of Alzheimer's disease, where remote interactions between amyloid in adjacent brain regions have not yet occurred and only latent tau exists in local regions, amyloid vaccines can be administered to prevent remote interactions between tau and amyloid present in specific regions. By administering an amyloid vaccine, future accumulation of amyloid and subsequent propagation of amyloid and tau due to remote interactions can be prevented. For patients with a certain degree of Alzheimer's disease progression, where remote interactions between amyloid in adjacent brain regions occur but local interactions between amyloid and tau in specific brain regions do not, amyloid-targeted therapeutics can be chosen. In this case, reducing the accumulation of amyloid in the patient's brain regions through amyloid-targeted therapeutics can prevent the subsequent propagation of modified tau to other brain regions. Additionally, when both remote interactions between amyloid and tau and local interactions between amyloid and tau occur simultaneously in a patient's brain, administering therapeutics targeting both amyloid and tau can improve symptoms and therapeutic efficacy for Alzheimer's disease. Thus, the occurrence of remote interactions between amyloid and tau, as well as local interactions between amyloid and tau, in patients with or suspected of having Alzheimer's disease can be criteria for selecting the optimal therapeutic agents for different stages of Alzheimer's disease progression. Therefore, assessing the presence of remote and local interactions between amyloid and tau in a subject is an important factor in the treatment process of Alzheimer's disease, and methods for determining these interactions will be described in detail in subsequent embodiments.

Figure 5:
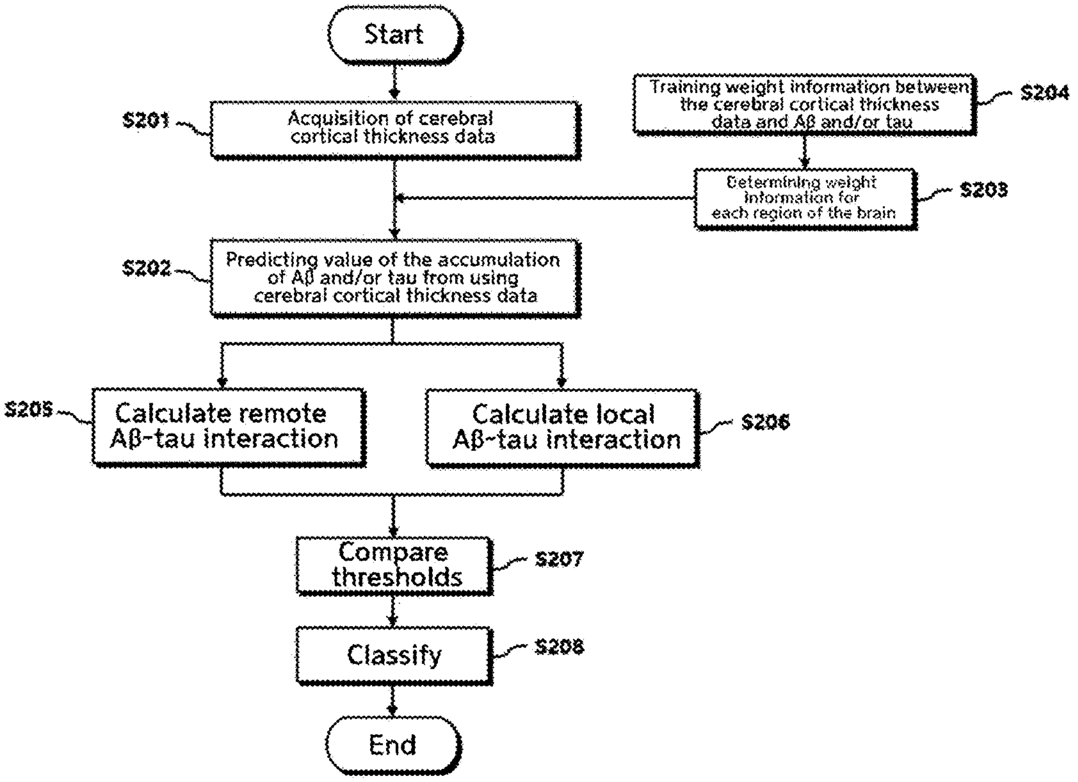
FIG. 5 is a block diagram illustrating the process of providing information for companion diagnostics for Alzheimer's disease treatments according to an embodiment of the present disclosure.
Figure 6:
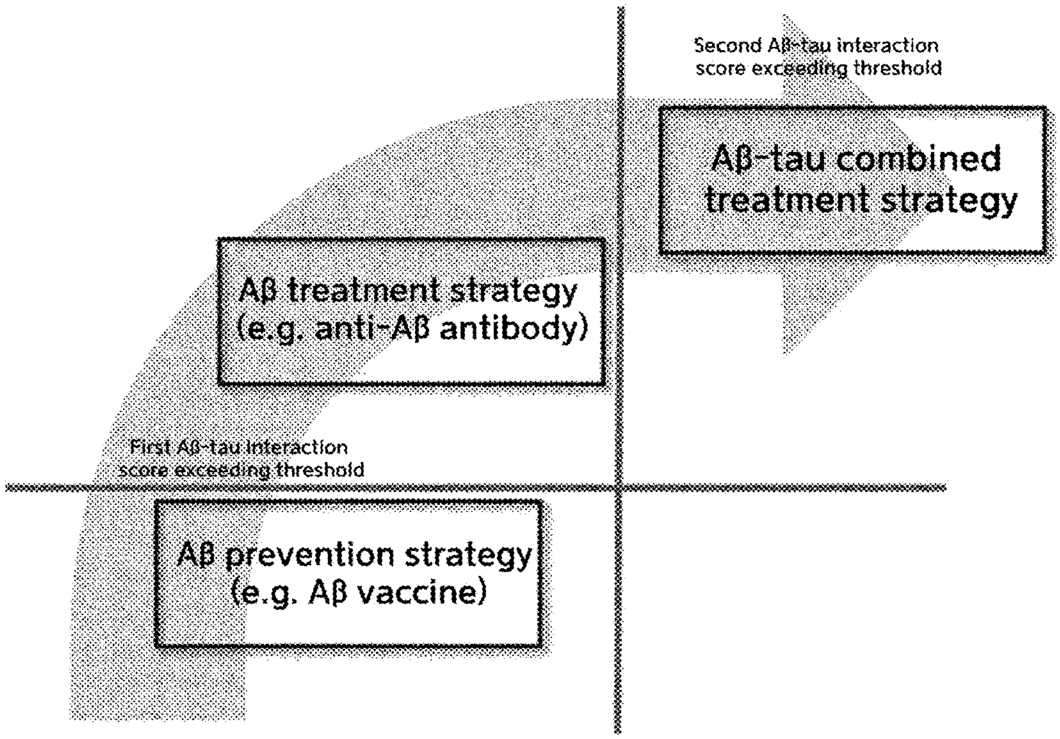
FIG. 6 is a diagram illustrating treatment strategies according to the progression of Alzheimer's disease.

FIG. 5 is a block diagram illustrating the process of providing information for companion diagnostics for Alzheimer's treatments according to an embodiment of the present disclosure, and FIG. 6 is a diagram illustrating treatment strategies according to the progression of Alzheimer's disease.

Referring to FIG. 5, the method for providing information for companion diagnostics for Alzheimer's disease treatments according to an embodiment of the present disclosure involves acquiring cerebral cortical thickness data, predicting the accumulation values of amyloid and/or tau, calculating the remote amyloid-tau interaction, calculating the local amyloid-tau interaction, and comparing the calculated interaction values with threshold values to classify the subject and determine the appropriate therapeutic agent.

Additionally, the method for providing information for companion diagnostics for Alzheimer's treatments according to an embodiment may further include a step of determining weight information for cerebral cortical thickness data and amyloid and/or tau.

Steps S201, S202, S203, and S204 may be performed in the same manner as the method for predicting the degree of Alzheimer's disease-related accumulation biomarkers according to an embodiment of the present disclosure as described above.

In step S205, the degree of remote interaction between amyloid and tau may be calculated. In step S205, a first amyloid-tau score quantifying the remote interaction between amyloid accumulated in the first brain region of the subject and amyloid accumulated in the adjacent third brain region, and the tau accumulation in the first brain region can be calculated. Specifically, step S205 can involve calculating a first amyloid-tau score from the amyloid interaction value quantifying the interaction between amyloid accumulated in the first brain region and amyloid accumulated in the adjacent third brain region, and the tau accumulation value in the first brain region. For example, the first amyloid-tau score can be calculated by summing the products of the amyloid interaction score, which is the sum of the products of the neural network strength and the amyloid accumulation values in the connected third brain region, and the tau accumulation value in the first brain region.

In an embodiment, the first amyloid-tau score can be calculated using the following mathematical formula 4:

$$RemInt_1 = (RemA_{1j}) \times (LocT_1) = \left(\sum^{m} \hat{\beta}_{1j} \cdot LocA_j\right) \times (LocT_1) \quad \text{[Mathematical Formula 4]}$$

(wherein, $RemInt_1$ is the remote Aβ-tau interaction score between the first brain region and the connected regions, $RemA_{1j}$ is the remote amyloid interaction degree between the first brain region and the connected regions, $\hat{\beta}_{ij}$ is the weight for the amyloid interaction between the first brain region and the connected regions, $LocA_j$ is the amyloid accumulation value in the regions connected to the first brain region, and $LocT_1$ is the tau accumulation value in the first brain region.)

The amyloid interaction value can be calculated from the amyloid accumulation values and the neural network weight values of the first and third brain regions. The neural network weight may be determined based on the connectivity value between the first and third brain regions.

The first brain region and the adjacent third brain region may be a single brain region or a set of multiple adjacent brain regions. Additionally, the first brain region and the second brain region may be either adjacent or non-adjacent.

In step S206, a second amyloid-tau score, which quantifies the local interaction between amyloid and tau in the second brain region, can be calculated from the accumulation values of amyloid and tau in the second brain region. Specifically, step S206 may be performed by calculating the second amyloid-tau score from the accumulation values of amyloid and tau in the second brain region of the subject. For example, the second amyloid-tau score can be calculated by multiplying the amyloid accumulation value by the tau accumulation value in the second brain region.

In an embodiment, step S206 may be adapted for calculating the second amyloid-tau score using the following mathematical formula 5:

$$LocInt_2 = (LocA_2) \times (LocT_2) \quad \text{[Mathematical Formula 5]}$$

(wherein, $LocInt_2$ is the local Aβ-tau interaction score in the second brain region, $LocA_2$ is the amyloid accumulation value in the second brain region, and $LocT_2$ is the tau accumulation value in the second brain region.).

In step S207, a process of comparing the remote amyloid-tau interaction score and the local amyloid-tau interaction score with threshold values may be performed. Specifically, comparison may be made between the remote amyloid-tau interaction score, that is, the first amyloid-tau score, and a first threshold value and between the local amyloid-tau interaction score, that is, the second amyloid-tau score, and a second threshold value.

At this point, the method for providing information for companion diagnostics for Alzheimer's treatments according to an embodiment may optionally include a step of calculating the first threshold value and the second threshold value, or may use predefined threshold values. When using predefined first and second threshold values, the given threshold values may be used to compare with the first amyloid-tau score or the second amyloid-tau score, respectively. When including the step of calculating threshold values, the first threshold value and the second threshold value may be calculated by multiplying the values that accurately distinguish between positive and negative amyloid and the values that accurately distinguish between positive and negative tau in relation to the first brain region or the second brain region. For example, the threshold value for a specific brain region can be calculated using the following mathematical formula 6:

$$IntCut_i = (CutA_i) \times (CutT_i) \quad \text{[Mathematical Formula 6]}$$

(wherein, $IntCut_i$ is the threshold value to compare with the Aβ-tau interaction degree in the i-th brain region, $CutA_i$ is the value that most accurately distinguishes in fact between positive and negative amyloid accumulation in the i-th brain region, and $CutT_i$ is the value that most accurately distinguishes in fact between positive and negative tau accumulation in the i-th brain region.)

In step S208, subjects can be classified into groups based on comparisons between the first amyloid-tau score and the first threshold value and between the second amyloid-tau score and the second threshold value.

Specifically, the extent of Alzheimer's disease progression in the subject and the optimal therapeutic agent can be determined based on whether the first and second amyloid-tau scores exceed or fall below the respective threshold values.

For instance, as shown in FIG. 6, the determination of a therapeutic agent based on the progression of Alzheimer's disease may involve assessing whether the first amyloid-tau score is below or above the first threshold value and whether the second amyloid-tau score is below or above the second threshold value. Referring additionally to FIG. 4 for detailed explanation, if the first amyloid-tau score does not exceed the first threshold value, it can be inferred that there is no remote interaction between amyloid and tau in the subject's first brain region, and the treatment strategy can primarily focus on preventing amyloid accumulation. Therefore, if the first amyloid-tau score does not exceed the first threshold value, the subject can be classified into the first group, and a therapeutic agent aimed at inhibiting amyloid accumulation, such as an amyloid vaccine, can be administered. If the first amyloid-tau score exceeds the first threshold value but the second amyloid-tau score is below the second threshold value, it can be inferred that remote interactions between amyloid and tau are occurring in the brain regions of the subject, but there are no local interactions between amyloid and tau in specific brain regions. The treatment strategy can then focus on removing accumulated amyloid. Therefore, if the first amyloid-tau score exceeds the first threshold value while the second amyloid-tau score is below the second threshold value, the subject can be classified into the second group, and a therapeutic agent aimed at removing accumulated amyloid, such as an anti-amyloid antibody, can be selected. If the second amyloid-tau score exceeds the second threshold value, it can be inferred that local interactions between amyloid and tau are occurring in specific brain regions of the subject. The treatment strategy can then focus on removing both accumulated amyloid and tau. Therefore, if the second amyloid-tau score exceeds the second threshold value, a therapeutic agent aimed at removing both accumulated amyloid and tau can be selected.

Below, a better understanding of the present disclosure may be obtained through the following examples, which are set forth to illustrate, but are not to be construed to limit, the present disclosure.

Example 1: Predicting the Global Accumulation Degree of Amyloid

An experiment was conducted using T1-weighted magnetic resonance imaging (MRI), positron emission tomography (PET) images, and demographic/clinical information provided by Gangnam Severance Hospital. The demographic information used included age, sex, and years of education.

The acquired PET images were used as baseline data, while the T1-weighted MRI images were used as follow-up data. Measurement was made of cerebral cortical thickness. In this regard, FreeSurfer software was used to generate the pial/white surface from the T1-weighted MRI images to extract the cortical part of the brain. The thickness of the cortical part was measured at each vertex position defined on the surface, and the average thickness for each brain region was calculated. The PET images were aligned with the corresponding T1-weighted MRI images taken from the same subject using a linear registration method. The standardized uptake value (SUV) for amyloid accumulation in each brain region was extracted, and the SUVR value was calculated as the ratio of the SUV to the value in the reference region.

To reflect the same importance for the cerebral cortical thickness and amyloid SUVR values, normalization was performed to derive the W-score. Specifically, the demographic information, that is, age, sex, years of education, was used as covariates for normalization, as shown in the following mathematical formula 7, using only the normal group for adjustment:

$$W-\text{score}_i = \frac{E_i - \hat{E}_i}{\sqrt{\text{Var}(E_{CN,i} - \hat{E}_{CN,i})}} \quad \text{[Mathematical Formula 7]}$$

(wherein, $E_i$ is the data to be standardized, including the cerebral cortical thickness and amyloid SUVR value in region i, $\hat{E}_i$ is the predicted data for region i using only the covariates through a regression model between covariates and values to be standardized in a normal group, and $\sqrt{\text{Var}(E_{CN,i}-\hat{E}_{CN,i})}$ is the residual standard deviation between the actual data for region i and the predicted values from the regression model in the normal group.)

Next, the weights between the standardized cerebral cortical thickness and amyloid accumulation values were determined using logistic regression analysis, specifically the logistic regression analysis according to the following mathematical formula 2. For logistic regression analysis, training was conducted using the standardized cerebral cortical thickness data (X) in each brain region as input to predict the amyloid positivity/negativity (Y) for the brain region. As many logistic regression models as the number of the brain regions were trained. Subsequently, the Beta (β) values and corresponding P-values of the trained logistic regression models were checked. Beta values with P-values below a specific threshold were used as weights.

$$H(X) = \frac{1}{1+e^{-(Wz+b)}} = \text{sigmoid}(Wx+b) = \sigma(Wx+b) \quad \text{[Mathematical Formula 2]}$$

(where sigmoid is a sigmoid function that produces an output value between 0 and 1 for any input value, W represents a weight that best fits the given data, and b represents the bias (intercept)).

After determining the weights, the amyloid accumulation degree was estimated, specifically using the following mathematical formula 8:

$$pX_i = \sum_{j=1}^{m} a_j \hat{\beta}_{ij} \quad \text{[Mathematical Formula 8]}$$

(wherein, $pX_i$ is the predicted accumulation degree of amyloid or tau, m is the number of selected brain regions, $a_j$ is the cerebral cortical thickness of the selected region, and $\hat{\beta}_{ij}$ is the weight for each region to be predicted for the accumulation value.)

After the determination of weights through mathematical formula 2, the performance of the prediction model was evaluated by creating a binary classifier to classify amyloid positivity/negativity based on the global amyloid accumulation degree, using 5-fold cross validation.

Figure 7:
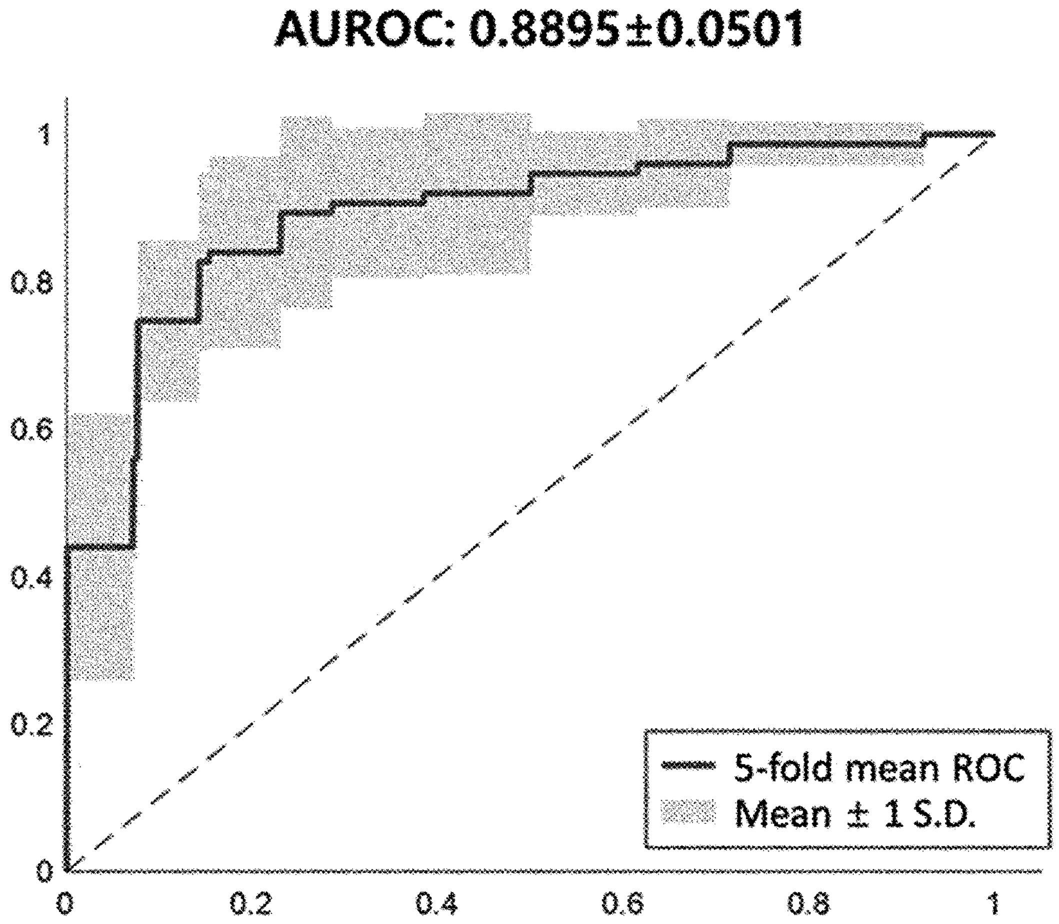
FIG. 7 is a diagram showing the results of evaluating the accuracy of the Alzheimer's disease-related biomarker prediction method according to an embodiment of the present disclosure using the area under the receiver operating characteristic curve (AUROC).

The area under the receiver operating characteristic curve (AUROC), which has been used as a method for evaluating the performance of binary classifiers, was calculated, yielding an average value of 0.8895, as shown in FIG. 7. This result confirmed that the method for predicting the amyloid accumulation degree according to an embodiment could accurately distinguish between amyloid-positive and amyloid-negative subjects across the entire brain.

Example 2: Estimating Amyloid and Tau Accumulation Degree by Region

An experiment was conducted using T1-weighted MRI, PET images, and demographic/clinical information obtained from Gangnam Severance Hospital. The demographic information included age, sex, and years of education, while the clinical information included Mini-Mental State Examination (MMSE) scores.

Similar to Example 1, cerebral cortical thickness was measured using T1-weighted MRI, and the accumulation values of amyloid and tau were measured using PET images SUVR and converted to values. The values were standardized using demographic information.

Subsequently, weights were determined between the standardized cerebral cortical thickness and the amyloid and tau accumulation values using correlation analysis. Specifically, partial correlation analysis was employed to select regions with correlation coefficients exceeding a certain value, and the correlation coefficients of the selected regions were used as weights.

In detail, the subjects were sorted in order of descending PET amyloid and tau SUVR values among the dataset possessed (Pseudo-longitudinal order sorting). The sorted subjects were screened using a window of fixed size while calculating the partial correlation between the PET amyloid and tau SUVR values and the cerebral cortical thickness for each brain region. The partial correlation calculated for each region every window was clustered into four stages of disease progression, taking the average of the partial correlations for each cluster. For each estimated region, the cluster with the highest correlation to the actual amyloid and tau accumulation degree was determined. The values of the regions connected to the clusters (regions with remaining values in the stage four) were used as the final weights.

The regions estimated for the amyloid accumulation degree included inferior temporal gyrus, precuneus, and caudal middle frontal gyrus while the regions estimated for the tau accumulation degree includes entorhinal cortex, inferior temporal gyrus, and inferior parietal lobule. After determining the weights, the amyloid and tau accumulation degrees were estimated using the determined weights in the same manner as in Example 1.

Figure 8:
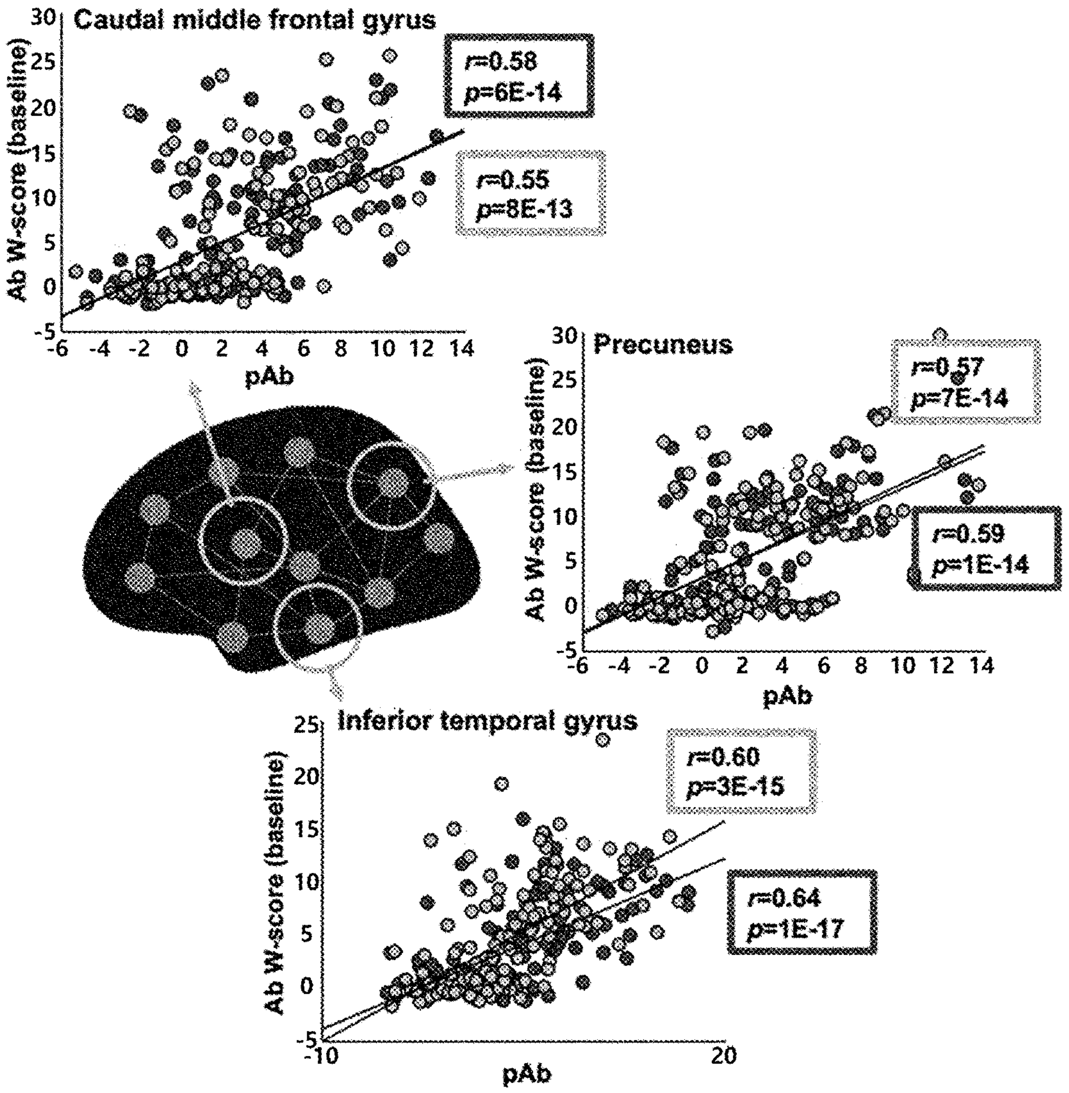
FIG. 8 shows diagrams illustrating the results of predicting the accumulation degree of amyloid in the inferior temporal gyrus, precuneus, and caudal middle frontal gyrus according to an embodiment of the present disclosure, and evaluating the accuracy thereof through correlation analysis.
Figure 9:
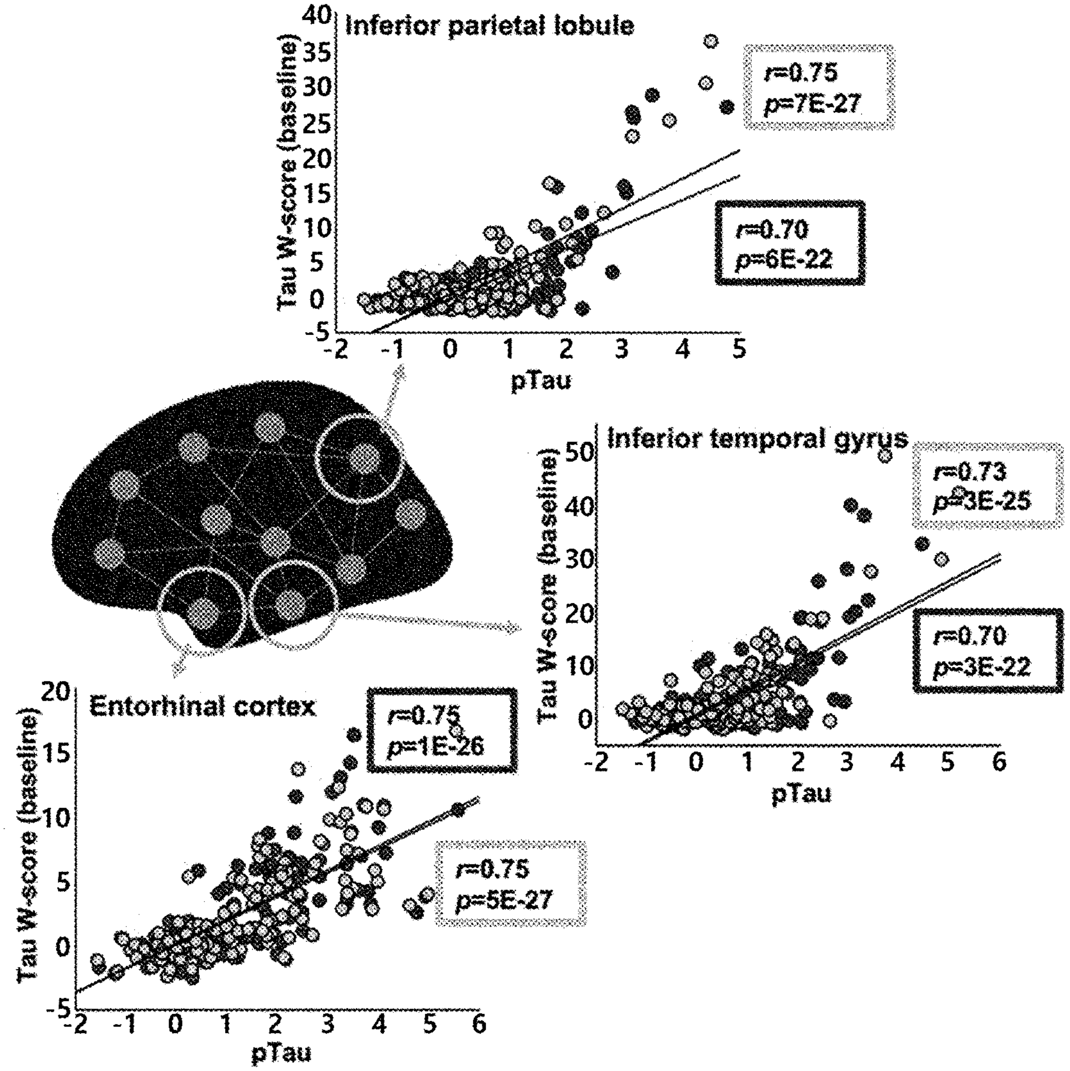
FIG. 9 shows diagrams illustrating the results of predicting the accumulation degree of tau in the entorhinal cortex, inferior temporal gyrus, and inferior parietal lobule according to an embodiment of the present disclosure, and evaluating the accuracy thereof through correlation analysis.

The estimated values were evaluated for performance by conducting correlation analysis between the actual amyloid and tau accumulation degrees and the estimated values derived from cerebral cortical thickness. The correlation analysis results are depicted in FIGS. 8 and 9. As estimated through the cerebral cortical thicknesses, the amyloid correlation coefficients were measured to be 0.62 on average for left/right hemispheres in the inferior temporal gyrus, 0.58 on average in the precuneus, and 0.57 on average in the caudal middle frontal gyrus. As for the tau correlation coefficients, their average values were measured to be 0.75 in the entorhinal cortex, 0.72 in the inferior temporal gyrus, and 0.73 in the inferior parietal lobule. These results confirmed that the method for estimating amyloid and tau accumulation degrees according to this embodiment achieved high accuracy.

Example 3: Predicting Efficacy of Alzheimer'S Disease Therapeutics and Determining Optimal Treatment An experiment was conducted to predict the efficacy of Alzheimer's disease therapeutics using the cerebral cortical thickness data, amyloid and tau accumulation values, and demographic/clinical information used in Example 2, along with the cerebral cortical thickness-amyloid weights and the estimated amyloid/tau accumulation values obtained in Example 2.

The amyloid and tau SUVR values obtained from actual PET images and the amyloid and tau SUVR values estimated from MRI were used to assess the interaction degree between amyloid and tau. Based on these interactions, subjects were classified into three groups: healthy controls (HC), amnestic mild cognitive impairment (aMCI), and Alzheimer's disease (AD).

The first brain region for assessing interaction was set as the inferior temporal gyrus (ITG), and the second brain region was set as the entorhinal cortex (EC). Specifically, the interaction degrees between amyloid and tau in the first and second brain regions were calculated using the following mathematical formulas 9 and 10:

[Mathematical Formula 9]

$$RemInt_1 = (RemA_{1j}) \times (LocT_1) = \left(\sum^{m} \hat{\beta}_{1j} \cdot LocA_j\right) \times (LocT_1)$$

(wherein, $RemInt_1$ is the remote Aβ-tau interaction score between the first brain region and the connected regions, $RemA_{1j}$ is the remote amyloid interaction degree between the first brain region and the connected regions, $\hat{\beta}_{1j}$ is the weight for the amyloid interaction between the first brain region and the connected regions, $LocA_j$ is the W-score of the amyloid SUVR value in the first brain region and connected regions, and $LocT_1$ is the W-score of the tau SUVR value in the first brain region.)

[Mathematical Formula 10]

$$LocInt_2 = (LocA_2) \times (LocT_2)$$

(wherein, $LocInt_2$ is the local Aβ-tau interaction score in the second brain region, $LocA_2$ is the W-score of the amyloid SUVR value in the second brain region, and $LocT_2$ is the W-score of the tau SUVR value in the second brain region.)

The weights $\hat{\beta}_{ij}$ for the amyloid interaction between the brain regions connected to the first brain region were calculated using the following process. The FSL toolbox was used to correct for eddy current effects and/or motion artifacts in the diffusion-weighted MRI. The T1-weighted MRI of the same subject, where brain regions were defined, was aligned to the diffusion-weighted MRI using inverse registration. Subsequently, the diffusion tensor imaging technique and deterministic tractography technique were applied using the Diffusion Toolkit to extract neural fibers and calculate the average fractional anisotropy value for all fibers connecting each pair of regions. The neural network strength value between the two brain regions was calculated. The average values for each region pair were normalized by dividing the sum of the values for all regions connected to a specific brain region by the total, yielding values between 0 and 1 used as weights. If more than one-third of the region pair values were missing, the region pair was considered not connected by a neural network.

Then, the amyloid and tau interaction scores calculated for the first brain region were compared with the first threshold value, and the interaction scores for the second brain region were compared with the second threshold value. These threshold values were calculated relative to the data distribution of healthy controls using the following mathematical formula 11:

$$IntCut_i = (CutA_i) \times (CutT_i) \quad \text{[Mathematical Formula 11]}$$

(wherein, $IntCut_i$ is the threshold value for comparison with the Aβ-tau interaction degree in the i-th brain region, $CutA_i$ is the W-score value that most accurately distinguishes between amyloid-positive and amyloid-negative SUVR values for the i-th brain region, and $CutT_i$ is the W-score value that most accurately distinguishes between tau-positive and tau-negative SUVR values for the i-th brain region.)

Figure 10:
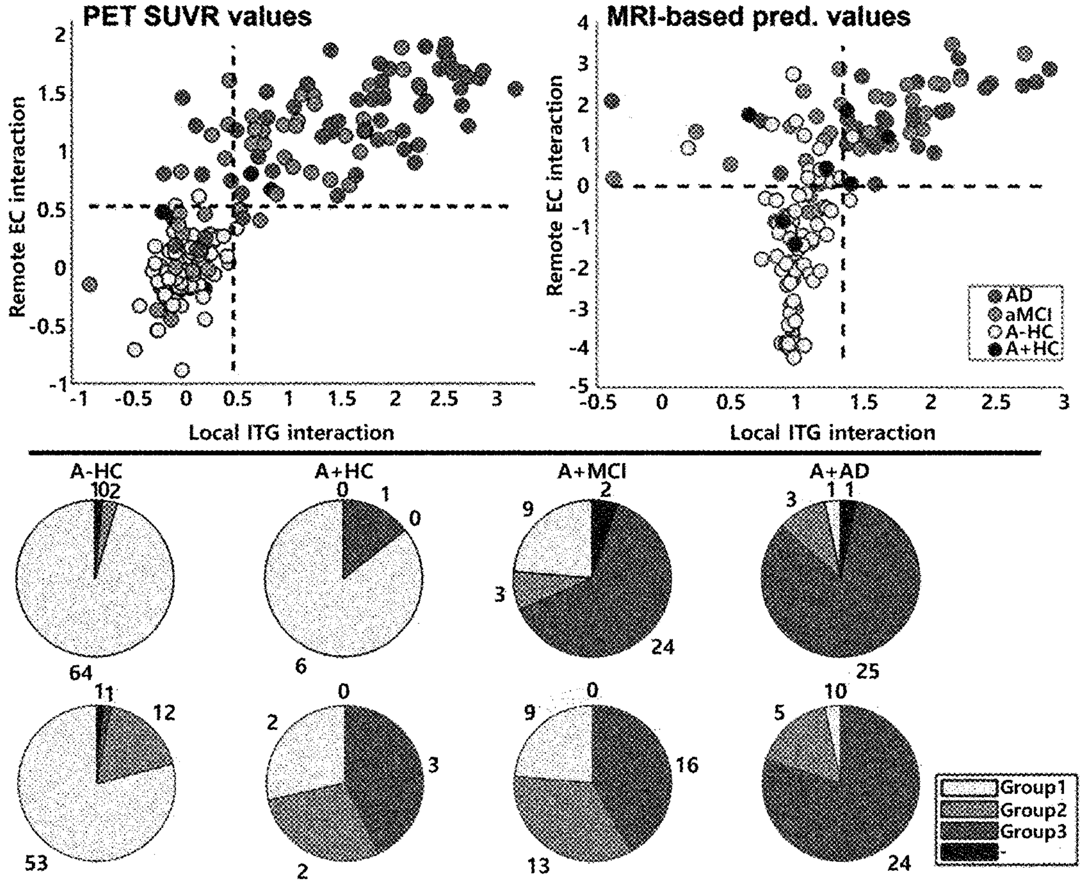
FIG. 10 shows diagrams illustrating the results of an experiment predicting the efficacy of Alzheimer's disease treatments according to an embodiment of the present disclosure.

As shown in FIG. 10, the proportion of Group 1 to Group 3 increases as the diagnostic status of the patient progresses from healthy controls (HC) to amnestic mild cognitive impairment (aMCI) to Alzheimer's disease (AD). Additionally, the experimental results showed minimal differences between actual and predicted values, confirming the accuracy of the model.

The various embodiments presented herein can be implemented as methods, devices, or manufactured articles using standard programming and/or engineering techniques. The term "manufactured article" includes any computer-readable storage device that can access a computer program, carrier, or media. Examples of computer-readable storage media include, but are not limited to, magnetic storage devices (e.g., hard disks, floppy disks, magnetic strips), optical disks (e.g., CDs, DVDs), smart cards, and flash memory devices (e.g., EEPROM, cards, sticks, key drives). Additionally, the various storage media presented here can include one or more devices and/or other machine-readable media for storing information.

It should be understood that the specific order or hierarchy of steps in the processes presented is an example of illustrative approaches. Based on design preferences, the specific order or hierarchy of steps in the processes can be rearranged within the scope of the present disclosure. The appended method claims provide elements of various steps in a sample order but are not meant to be limited to the specific order or hierarchy presented.

The description of the presented embodiments is provided to enable any person skilled in the art to utilize or implement the present disclosure. Various modifications to these embodiments will be apparent to those skilled in the art, and the general principles defined herein can be applied to other embodiments without departing from the scope of the present disclosure. Therefore, the present disclosure should not be limited to the embodiments shown but should be given the broadest scope consistent with the principles and novel features disclosed.

The invention claimed is:

1. A method for providing information for companion diagnostics related to Alzheimer's disease treatments and treating Alzheimer's disease using medical imaging, the method comprising:

acquiring, by a data acquisition processor, first cerebral cortical thickness data for a plurality of brain regions of a subject, said plurality of brain regions comprising at least a first brain region, a second brain region, and a third brain region, from magnetic resonance imaging (MRI) data of the brain of the subject processed to obtain cortical thickness data for respective cortical regions;

calculating, by a prediction processor executing a trained neural network model, predicted values of amyloid and tau accumulation in each of the plurality of brain regions of the subject from the first cerebral cortical thickness data by using weight information defined between at least one set of second cerebral cortical thickness data and at least one set of amyloid-tau data;

a first calculation operation executed by the prediction processor of calculating a first amyloid-tau score from an amyloid interaction value and the predicted value of tau accumulation in the first brain region, wherein the amyloid interaction value scores the interaction between the predicted value of amyloid accumulated in the first brain region and the predicted value of amyloid accumulated in the third brain region adjacent to the first brain region, and the tau predicted value in the first brain region;

a second calculation operation executed by the prediction processor of calculating a second amyloid-tau score from the predicted values of amyloid and tau in the second brain region of the subject;

a first comparison operation executed by the prediction processor of comparing the first amyloid-tau score with a first threshold value that distinguishes between positive and negative amyloid and tau in the first brain region; and a second comparison operation executed by the prediction processor of comparing the second amyloid-tau score with a second threshold value that distinguishes between positive and negative amyloid and tau in the second brain region;

a classification step of classifying the subject into group 1 if the first amyloid-tau score is less than or equal to the first threshold value, group 2 if the first amyloid-tau score exceeds the first threshold value and the second amyloid-tau score is less than or equal to the second threshold value, and group 3 if the second amyloid-tau score exceeds the second threshold value; and administering an amyloid vaccine to the subject when classified into group 1, administering an anti-amyloid antibody to the subject when classified into group 2, or administering a therapeutic agent targeting both amyloid and tau to the subject when classified into group 3.

2. The method of claim 1, wherein the amyloid interaction value is calculated from the predicted values of amyloid accumulation in the first brain region and the third brain region and neural network weight values, and the neural network weight values are derived from a strength of a neural network between the first brain region and the third brain region.

3. The method of claim 1, further comprising a determination step of deriving a degree of association between the second cerebral cortical thickness data and the amyloid-tau data to determine the weight information.

4. The method of claim 3, wherein the determination step comprises a learning step of extracting and learning the weight information based on the second cerebral cortical thickness data and the amyloid-tau data using machine learning.

* * * * *